(12) United States Patent
Kuechler et al.

(10) Patent No.: US 7,115,789 B2
(45) Date of Patent: Oct. 3, 2006

(54) PROCESS FOR REMOVAL OF ALKYNES AND/OR DIENES FROM AN OLEFIN STREAM

(75) Inventors: Keith Holroyd Kuechler, Friendswood, TX (US); David R. Lumgair, Jr., Craddockville, VA (US)

(73) Assignee: Exxon Mobil Chemical Patents Inc., Houston, TX (US)

( * ) Notice: Subject to any disclaimer, the term of this patent is extended or adjusted under 35 U.S.C. 154(b) by 558 days.

(21) Appl. No.: 10/403,229

(22) Filed: Mar. 28, 2003

(65) Prior Publication Data

US 2004/0192982 A1 Sep. 30, 2004

(51) Int. Cl.
*C07C 5/08* (2006.01)
*C07C 5/09* (2006.01)

(52) U.S. Cl. .................. 585/265; 585/259
(58) Field of Classification Search ............... 585/265, 585/259
See application file for complete search history.

(56) References Cited

U.S. PATENT DOCUMENTS

| | | | |
|---|---|---|---|
| 3,792,981 A | 2/1974 | Hettick et al. | 23/288 R |
| 4,234,410 A | 11/1980 | Kelley | 208/57 |
| 4,831,200 A * | 5/1989 | Debras et al. | 585/259 |
| 4,940,687 A | 7/1990 | Liu et al. | 502/333 |
| 5,510,550 A | 4/1996 | Cheung et al. | 585/259 |
| 5,811,621 A | 9/1998 | van Dijk | 585/639 |
| 5,856,262 A | 1/1999 | Flick et al. | 502/328 |
| 6,107,533 A | 8/2000 | Vebeliunas et al. | 585/259 |
| 6,297,414 B1 | 10/2001 | Barchas et al. | 585/259 |
| 6,410,811 B1 | 6/2002 | Chau et al. | 585/259 |
| 6,576,588 B1 * | 6/2003 | Ryu et al. | 502/331 |
| 2002/0007101 A1 | 1/2002 | Senetar et al. | 585/809 |
| 2002/0022754 A1 | 2/2002 | Boyer et al. | 585/265 |
| 2002/0165092 A1 | 11/2002 | Zhang et al. | 502/330 |

FOREIGN PATENT DOCUMENTS

| | | |
|---|---|---|
| EP | 0 523 482 | 1/1993 |
| FR | 2 597 113 | 10/1987 |
| WO | WO 94/04477 | 3/1994 |

* cited by examiner

*Primary Examiner*—Thuan D. Dang (57) ABSTRACT

The present invention is a process for removing alkynes and/or dienes from an olefin product stream withdrawn from an oxygenate-to-olefins reactor. The process comprises hydrogenating a first olefin stream that has alkynes and/or dienes in the presence of excess hydrogen and a first hydrogenation catalyst. The hydrogenation of the first olefin stream produces a second olefin stream that has unreacted hydrogen. The second olefin stream is contacted with a second hydrogenation catalyst producing a third olefin stream. The third olefin stream has low levels of hydrogen and alkynes and/or dienes.

34 Claims, 1 Drawing Sheet

PROCESS FOR REMOVAL OF ALKYNES AND/OR DIENES FROM AN OLEFIN STREAM

FIELD OF THE INVENTION

The present invention relates to a process for removal of alkynes and/or dienes from an olefin stream, particularly an olefin stream from an oxygenate-to-olefins reaction.

BACKGROUND OF THE INVENTION

Olefins are traditionally produced from petroleum feedstock by catalytic or steam cracking processes. These cracking processes, especially steam cracking, produce prime olefins such as ethylene and/or propylene from a variety of hydrocarbon feedstock. Ethylene and propylene are important commodity petrochemicals useful in many processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, can be converted into prime olefins. This process is referred to as the oxygenate-to-olefin process. The preferred oxygenate for prime olefin production is methanol. The process of converting methanol-to-olefins is called the methanol-to-olefins process.

There are numerous technologies available for producing oxygenates, and particularly methanol, including fermentation or reaction of synthesis gas derived from natural gas, petroleum liquids, carbonaceous materials including coal, recycled plastics, municipal waste or any other organic material. The most common process for producing methanol is a two-step process of converting natural gas to synthesis gas. Then, synthesis gas is converted to methanol.

Generally, the production of synthesis gas involves a combustion reaction of natural gas, mostly methane, and an oxygen source into hydrogen, carbon monoxide and/or carbon dioxide. Synthesis gas production processes are well known, and include conventional steam reforming, autothermal reforming or a combination thereof.

Synthesis gas is then processed into methanol. Specifically, the components of synthesis gas (i.e., hydrogen, carbon monoxide and/or carbon dioxide) are catalytically reacted in a methanol reactor in the presence of a heterogeneous catalyst. For example, in one process, methanol is produced using a copper/zinc oxide catalyst in a water-cooled tubular methanol reactor.

The methanol is then converted to olefins in a methanol-to-olefins process and produces a reactor effluent stream. The reactor effluent stream contains desirable olefin product as well as byproducts. The byproducts are typically removed from any olefin product stream to make olefin product streams that are of an acceptable level of purity. Common byproducts in a methanol-to-olefin reactor effluent stream include several alkynes and/or dienes. Examples of alkynes and/or dienes include, but are not limited to, acetylene, methyl acetylene and propadiene. Alkynes and/or dienes are converted to olefins by a hydrogenation reaction. In a hydrogenation reaction, equimolar amounts of hydrogen and alkynes and/or dienes are reacted to produce a mole of olefin. The hydrogenation of olefin is a competing reaction whereby equimolar amounts of hydrogen and olefin are converted to a mole of paraffin. The reaction of alkyne to olefin is desirable because it eliminates an impurity, specifically the alkyne. The competing reaction is not desirable because it converts prime olefin product to less desirable paraffin byproduct.

Hydrogen, a reactant in the hydrogenation reaction, is often added to the alkyne containing olefin product stream to facilitate the reaction. Hydrogen is an impurity. Moreover, hydrogen often contains methane, CO and $CO_2$. Likewise, these impurities can contaminate the olefin product stream, even when the hydrogenation reaction consumes all of the hydrogen. An added step of fractionation (typically a stripper) is required after hydrogenation to remove, excess hydrogen, methane, carbon monoxide and/or carbon dioxide from the olefin product stream after hydrogenation.

It would be desirable to have a hydrogenation step to eliminate alkynes and/or dienes that would result in an olefin product stream that has acceptable levels of alkynes and/or dienes, hydrogen, methane, carbon dioxide and/or carbon monoxide without the need for an additional fractionation step. It would likewise be desirable to hydrogenate as much of the alkynes and/or dienes as possible while hydrogenating as little olefin as possible. The present invention satisfies these and other needs.

SUMMARY OF THE INVENTION

The present invention is a process for removing byproducts selected from the group comprising alkynes, dienes and mixtures thereof from an olefin product stream withdrawn from an oxygenate-to-olefins reactor. The process comprises hydrogenating a first olefin stream that contains olefins and byproducts. The hydrogenating occurs in the presence of excess hydrogen and a first hydrogenation catalyst. For the purpose of this document, excess hydrogen means more than equamolar amounts of hydrogen compared to the total moles of such byproducts. The process produces a second olefin stream that has unreacted hydrogen. The second olefin stream is contacted with a second hydrogenation catalyst producing a third olefin stream. The third olefin stream has less than specification levels of hydrogen and such byproducts. By specification levels it is meant the maximum amount of a byproduct that is tolerated in an olefin product that is used for a particular application or use. In one embodiment, the third olefin stream comprises 10 mppm or less hydrogen and about 1 mppm or less of such byproducts based upon the composition of the third olefin stream.

In another embodiment, there is a process for making a polyolefin product from an oxygenate feed stream. The process begins by contacting an oxygenate feed stream with a molecular sieve catalyst in an oxygenate-to-olefin reactor. The contacting step produces a first olefin stream having olefins and byproducts selected from the group comprising alkynes, dienes and mixtures thereof. The quantity of such byproducts in the first olefin stream is about 200 mppm or less of such byproducts for every mole of olefin in the first olefin stream. Typically, excess hydrogen is added to the first olefin stream. The mole ratio of hydrogen to such byproducts in the first product stream is about 1.05:1 or greater. The first olefin stream is hydrogenated in the presence of a first hydrogenation catalyst producing a second olefin stream. The second olefin stream comprises olefins and unreacted hydrogen. The second olefin stream is contacted with a second hydrogenation catalyst producing a third olefin stream. The third olefin stream has about 10 mppm or less hydrogen based upon the composition of the third olefin stream. The third olefin stream, then, is converted to the polyolefin product. In a certain embodiment, about 1 mppm or less olefins, based upon the total amount of olefins in the first olefin stream are hydrogenated in the foregoing process.

In another embodiment, there is a process for producing an ethylene stream from an oxygenate feed stream. The process comprises the step of contacting the oxygenate feed stream with a molecular sieve catalyst in a reactor. The contacting step produces a first olefin stream having ethylene, higher boiling point compounds and acetylene. The term "higher boiling point compounds" as it refers to ethylene means compounds with a boiling point higher than ethylene. A majority of the ethylene and a majority of the acetylene are separated from a majority of the higher boiling point compounds producing a first ethylene stream. The first ethylene stream is hydrogenated in the presence of excess hydrogen producing a second ethylene stream. The second ethylene stream comprises unreacted hydrogen. The unreacted hydrogen in the second ethylene stream is reacted to produce a third ethylene stream. The third ethylene stream has about 10 mppm or less hydrogen based upon the composition of the third ethylene stream. Moreover, about 1 mol. % or less of the ethylene in the first olefin stream is hydrogenated, based upon the amount of ethylene in the first ethylene stream.

In another embodiment, there is a process for producing a propylene stream from an oxygenate feed stream. The process comprises the step of contacting the oxygenate feed stream with a molecular sieve catalyst in a reactor. The contacting produces a first olefin stream having propylene, higher boiling point compounds or lower boiling point compounds and byproducts selected from the group comprising methyl acetylene, propadiene and mixtures thereof. The term "higher boiling point compounds" as it refers to propylene means compounds with a boiling point higher than propylene. The term "lower boiling point compounds" as it refers to propylene means compounds with a boiling point lower than propylene. A majority of the propylene and a majority of said byproducts are separated from a majority of the higher boiling point compounds or lower boiling point compounds producing a first propylene stream. The first propylene stream is hydrogenated in the presence of excess hydrogen producing a second propylene stream. The second propylene stream comprises unreacted hydrogen. The unreacted hydrogen in the second propylene stream is reacted to produce a third propylene stream. The third propylene stream has less than 10 mppm hydrogen based upon the composition of the third propylene stream. Moreover, no more than 1 mol. % of the propylene in the first olefin stream is hydrogenated in the previous hydrogenation steps, based upon the amount of propylene in the first propylene stream.

In another embodiment, there is a process for hydrogenating byproducts consisting of alkynes, dienes and mixtures thereof in an olefin product stream from an oxygenate-to-olefin reactor. The process comprises providing an olefin stream comprising byproducts and olefin selected from the group consisting of ethylene, propylene and mixtures thereof. Excess hydrogen is added to the olefin stream. At least a portion of the excess hydrogen is from a hydrogen source stream that has about 0.2 mol. % or less $CO_2$ and/or CO and has about 10 mol. % or less methane. The olefin stream is hydrogenated to produce a hydrogenated olefin stream. The hydrogenated olefin stream has about 20 mppm or less hydrogen based upon the composition of the hydrogenated olefin stream. Optionally, the hydrogenated olefin stream is fractionated to remove methane.

According to one or embodiments including those previously set forth, at least a portion of the excess hydrogen is from a hydrogen source stream. The hydrogen source stream has about 90 mol. % or more, 95 mol. % or more or about 98 mol. % or more hydrogen based upon the composition of the hydrogen source stream. According to one or more embodiments including those previously set forth, a combined stream of the first olefin stream and the hydrogen source stream has about 500 mppm or less methane based upon the composition of the combined stream. Additionally or optionally, a combined stream of the first olefin stream and the hydrogen source stream has about 1 mppm or less CO based upon the composition of the combined stream. Additionally or optionally, the combined stream of the first olefin stream and the hydrogen source stream has about 1 mppm or less $CO_2$ based upon the composition of the combined stream. Moreover, the first olefin stream has about 1 mppm or less $CO_2$ based upon the composition of the first olefin stream in one embodiment.

In yet another embodiment, including one or more of the embodiments previously disclosed, the excess hydrogen is present in the first olefin stream or combined stream, preferably about 1.05 moles or more of hydrogen, more preferably about 1.5 moles to about 50 moles of hydrogen more preferably from about 1.5 moles to about 10 moles of hydrogen are present for every mole of such byproduct in the respective first olefin stream or combined stream.

In yet another embodiment that encompasses one or more of the embodiments previously discussed, the hydrogen source stream is from a source selected from the group comprising pipeline hydrogen, hydrogen from reformed naphtha, hydrogen from refinery streams, hydrogen from bottled sources, hydrogen from water electrolysis reactors, hydrogen from refinery streams and hydrogen from decomposition of oxygenates such as methanol.

In yet another embodiment that encompasses one or more of the embodiments previously discussed, the first olefin stream is heated. Typically, the first olefin stream is heated with the third olefin stream in a heat exchanger. Preferably, the first olefin stream is heated to a temperature ranging from about 100° F. (38° C.) to about 250° F. (121° C.)—more preferably from about 120° F. (49° C.) to about 200° F. (93° C.), most preferably from about 150° F. (66° C.) to about 190° F. (88° C.).

In yet another embodiment, including one or more embodiments selected from the embodiments disclosed above, the first hydrogenation step occurs at a pressure ranging from about 50 psia (344 kPaa) to about 400 psia (2760 kPaa), preferably from about 200 psia (1380 kPaa) to about 300 psia (2070 kpaa), more preferably from about 250 psia (1720 kpaa) to about 300 psia (2070 kPaa).

In another embodiment in combination with one or more of the embodiments selected above, the first catalyst is an elemental Group VIII metal catalysts. Preferably, the first catalyst is an elemental noble metal on a substrate comprising silica, alumina and mixtures thereof with a co-catalyst selected from the group consisting of elemental silver, vanadium, iodine and combinations thereof. More preferably, the first catalyst is an elemental palladium catalyst. Most preferably, the first catalyst is an elemental palladium catalyst on a substrate selected from the group comprising alumina, silica and mixtures thereof with a co-catalyst selected from the group consisting of elemental silver, vanadium, iodine and combinations thereof.

In one or more embodiments disclosed above the process alternatively or optionally has a first olefin stream that contains about 50 mol. % or more, preferably about 90 mol. % or more, more preferably about 98 mol. % or more olefin based upon the composition of the first olefin stream.

Optionally or alternatively, the first olefin stream comprises about 200 mppm or less alkynes and or dienes.

In another embodiment that is in combination with one or more of the embodiments disclosed above, the first olefin stream contains about 25 mol. % or more, preferably about 90 mol. % or more, more preferably about 98 mol. % or more ethylene based upon the composition of the first olefin stream. Optionally or alternatively, thy byproducts include acetylene. The first olefin stream comprises about 500 mppm or less, preferably about 200 mppm or less byproducts based upon the composition of the first olefin stream.

In another embodiment that is in combination with one or more of the embodiments disclosed above, the first olefin stream contains about 25 mol. % or more, preferably about 90 mol. % or more, more preferably about 98 mol. % or more propylene based upon the composition of the first olefin stream. Optionally or alternatively, the byproducts are selected from the group comprising methyl acetylene, propadiene and mixtures thereof. The first olefin stream comprises about 500 mppm or less, preferably about 200 mppm or less such byproducts based upon the composition of the first olefin stream.

In yet another embodiment that encompasses one or more of the embodiments previously discussed, the second olefin stream is heated. Preferably, the second olefin stream is heated to a temperature ranging from about 100° F. (38° C.) to about 250° F. (121° C.)—more preferably from about 120° F. (49° C.) to about 200° F. (93° C.), most preferably from about 150° F. (66° C.) to about 190° F. (88° C.).

In yet another embodiment, including one or more embodiments selected from the embodiments disclosed above, the second hydrogenation step occurs at a pressure ranging from about 50 psia (344 kPaa) to about 400 psia (2760 kPaa), preferably from about 200 psia (1380 kPaa) to about 300 psia (2070 kPaa), more preferably from about 250 psia (1720 kPaa) to about 300 psia (2070 kPaa).

In another embodiment in combination with one or more of the embodiments selected above, the second catalyst is an elemental Group VIII metal catalysts. Preferably, the second catalyst is an elemental noble metal on a substrate comprising silica alumina and mixtures thereof with a co-catalyst selected from the group consisting of elemental iron, elemental nickel and mixtures thereof. More preferably, the second catalyst is an elemental palladium catalyst. Most preferably, the second catalyst is an elemental palladium catalyst on substrate selected from the group comprising silica, alumina and mixtures thereof with a co-catalyst selected from the group consisting of elemental iron, elemental nickel and mixtures thereof. In one embodiment, the first catalyst is the same as the second catalyst. Preferably the first hydrogenation step occurs in a first bed of a reactor vessel and the second hydrogenation step occurs in a second bed of a reactor vessel.

DETAILED DESCRIPTION OF THE INVENTION

Introduction and Overview

Figure 1:
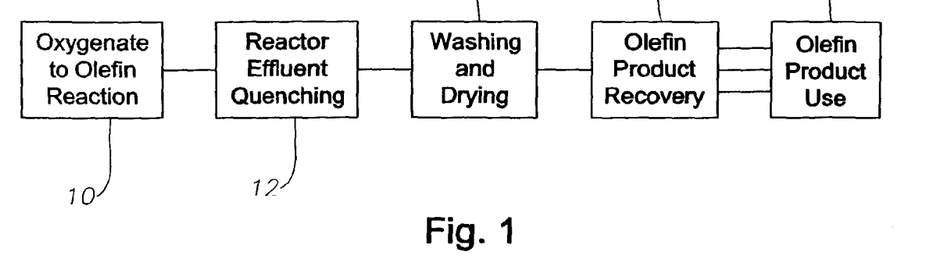
FIG. 1 illustrates the overall process of an oxygenate-to-olefins plant according to one embodiment of the present invention.

To aid in the understanding of the present invention, a brief overview of the stages of producing and using one or more olefin products from an oxygenate feed stream is discussed with reference to FIG. 1. The oxygenate-to-olefin reaction stage 10 occurs in an oxygenate-to-olefin reactor and converts an oxygenate feed stream into a gaseous output stream comprising one or more olefin(s). The gaseous output stream of an oxygenate-to-olefin reactor is defined as the effluent stream. The reactor effluent stream is particularly the gaseous output stream from the point this stream leaves the reactor to the point the stream enters a quench device.

Following the oxygenate-to-olefin reaction stage, the reactor effluent stream passes through an effluent quenching stage 12. The effluent quenching stage 12 cools the reactor effluent stream and removes water and catalyst fines from the reactor effluent stream. Included in the effluent quenching stage 12 is optional compression of the quenched effluent stream.

The quenched effluent stream then undergoes a washing and drying stage 14 to produce a dried effluent stream. Washing the quenched effluent stream removes acid components of the effluent stream, such as $CO_2$. Drying removes water that is saturated in the quenched effluent stream. Optionally, the washing and drying stage includes processing steps to remove additional oxygenates.

Figure 2:
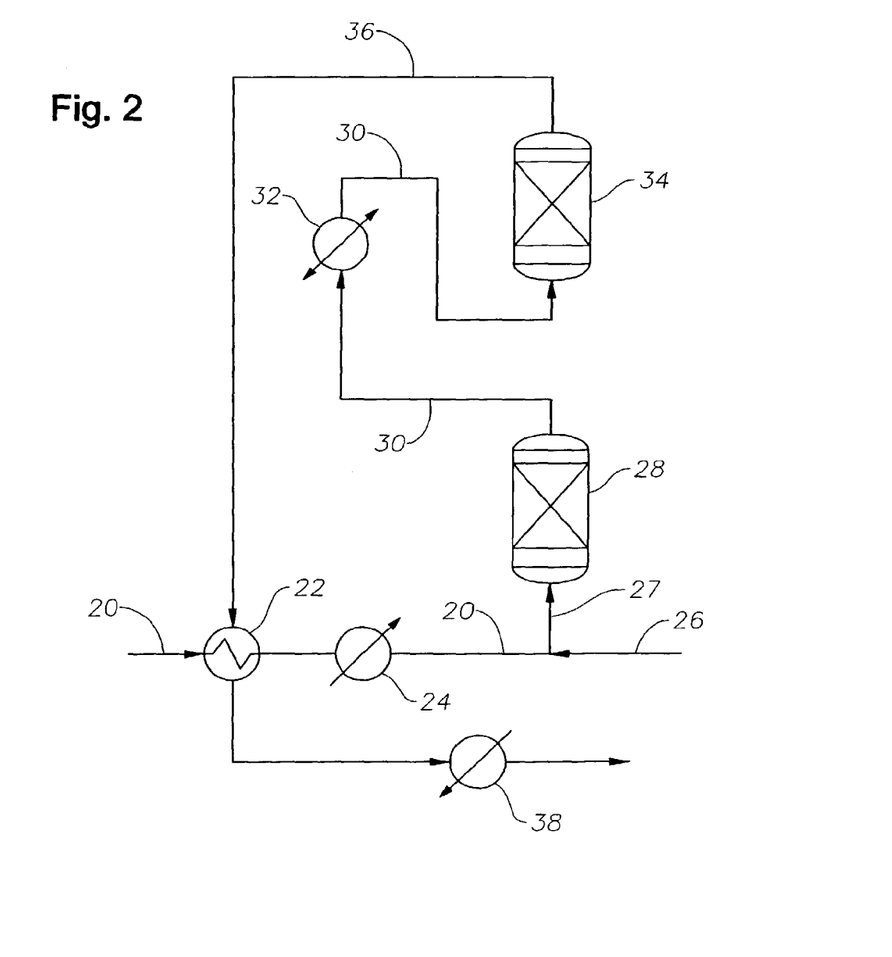
FIG. 2 is a process flow diagram illustrating an embodiment of the hydrogenation process according to the present invention.

The dried effluent stream then undergoes an olefin product recovery stage 16. Particularly, prime olefins, i.e. ethylene, propylene, and butylene are recovered in olefin product streams in acceptable grades of purity for their particular applications or end uses. In the product recovery stage 16, alkynes and/or dienes such as acetylene or methyl acetylene and/or propadiene is removed from an olefin stream according to one embodiment of the invention that is illustrated in FIG. 2. As used herein, "and/or" as it pertains to one or more compositions is defined as any composition comprising one of the compositions and any combination or mixture of the one or more compositions.

Finally, the olefin product streams pass through an olefin product use stage 18. In the olefin product use stage 18, the particular olefin product streams are used in a polymerization process to make polyolefin products in one embodiment. For a more complete understanding of the integrated process of producing and using olefin product streams from an oxygenate feed stream is discussed below in greater detail.

The Oxygenate-to-Olefin Reaction

An oxygenate feed stream is fed into an oxygenate-to-olefin reactor producing a reactor effluent stream. The oxygenate-to-olefin reactor is a reactor that uses a catalyst and particularly a molecular sieve catalyst to convert an oxygenate to an olefin. A molecular sieve catalyst is a catalyst made of a molecular sieve material as set forth herein. Molecular sieve catalysts are useful for converting a feed stream that contains one or more aliphatic-containing compounds. The one or more aliphatic-containing compounds include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feed stream is an oxygenate feed stream. Particularly, an oxygenate feed stream is a feed stream that comprises one or more organic compound(s) containing at least one oxygen atom. In the most preferred embodiment of the invention, the oxygenate in the oxygenate feed stream is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols that are useful in the oxygenate feed stream include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the oxygenate feed stream comprises oxygenates selected from one or more of methanol, ethanol, dimethyl ether, diethyl ether or a combination thereof, more preferably methanol and dimethyl ether, and most preferably methanol.

In one embodiment, the oxygenate feed stream is produced from an integrated process for producing oxygenates, particularly alcohols, from a hydrocarbon feedstock, preferably a hydrocarbon gas feedstock, more preferably methane and/or ethane. The first step in the process is passing the gaseous hydrocarbon feedstock, preferably in combination with a water stream, to a synthesis gas production zone to produce a synthesis gas stream containing synthesis gas. Synthesis gas production is well known, and typical synthesis gas temperatures are in the range of from about 700° C. to about 1200° C. and synthesis gas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas.

Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide, nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol. This purified oxygenate containing stream is used in one embodiment as the oxygenate feed stream. Non-limiting examples of a process for producing an oxygenate feed stream from hydrocarbons and using it to produce olefins is described in EP-B-0 933 345, which is herein fully incorporated by reference.

The feed stream, preferably an oxygenate feed stream, in one embodiment, contains one or more diluents, typically used to reduce the concentration of the active ingredients in the feed stream, and are generally non-reactive to the active ingredients in the feed stream or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feed stream entering into a reactor or added directly into the reactor, or added with a molecular sieve catalyst composition. In one embodiment, the amount of diluent in the feed stream is in the range of from about 1 to about 99 mole percent, preferably from about 1 to 80 mole percent, more preferably from about 5 to about 50, and most preferably from about 5 to about 25 diluent based on the total number of moles of the active components of the feed stream plus diluent in the feed stream.

In one embodiment, other hydrocarbons are added to the feed stream, preferably oxygenate feed stream, either directly or indirectly, and include olefin(s), paraffin(s), aromatic(s) (see for example U.S. Pat. No. 4,677,242, addition of aromatics) or mixtures thereof, preferably propylene, butene, pentene, and other hydrocarbons having 4 or more carbon atoms, or mixtures thereof.

The various feed streams, preferably oxygenate feed streams, discussed above are converted primarily into one or more olefin(s). The olefin(s) or olefin monomer(s) produced from the feed stream typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or non-conjugated dienes, polyenes, vinyl monomers and cyclic olefins.

In the most preferred embodiment, the feed stream, preferably an oxygenate feed stream, is converted in the presence of a molecular sieve catalyst composition into olefin(s) having 2 to 6 carbons atoms, preferably 2 to 4 carbon atoms. Most preferably, the olefin(s), alone or combination, are converted from an oxygenate feed stream preferably containing an alcohol, and most preferably methanol, to the preferred olefin(s) ethylene propylene and/or butylene often referred to as prime olefin(s).

The most preferred oxygenate-to-olefins process is the methanol-to-olefins process. In a methanol-to-olefin process, a methanol containing feed stream is converted to olefins in the presence of a methanol-to-olefins catalyst or catalyst composition. In one embodiment, the methanol-to-olefins catalyst or catalyst composition is molecular sieve catalyst composition.

In one embodiment of the process for conversion of an oxygenate feed stream, the amount of olefin(s) produced based on the total weight of hydrocarbon produced is greater than 50 weight percent, preferably greater than 60 weight percent, more preferably greater than 70 weight percent, and most preferably greater than 75 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

As noted, oxygenate-to-olefin processes use molecular sieve catalysts or molecular sieve catalyst compositions. The molecular sieve catalysts compositions have molecular sieve and binder and/or matrix material. The molecular sieve catalysts are prepared according to techniques that are known to a person of ordinary skill in the art.

Molecular sieves include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, AFO, AEL, EUO, HEU, FER, MEL, MFI, MTW, MTT, TON, EMT, FAU, ANA, BEA, CFI, CLO, DON, GIS, LTL, MER, MOR, MWW and SOD and substituted forms thereof; and the large pore molecular sieves. Preferably the molecular sieve is a zeolitic or zeolitic-type molecular sieve. Alternatively, the preferred molecular sieve is an aluminophosphate (ALPO) molecular sieves and/or silicoaluminophosphate (SAPO) molecular sieves and substituted, preferably metal substituted, ALPO and/or SAPO molecular sieves including the molecular sieves that are intergrowth materials having two or more distinct phases of crystalline structures within one molecular sieve composition.

Binder materials that are useful alone or in combination include various types of hydrated alumina, silicas, and/or other inorganic oxide sol. In one embodiment, the binders are alumina sols including include Nalco 8676 available from Nalco Chemical Co., Naperville, Ill., and Nyacol available from The PQ Corporation, Valley Forge, Pa.

Matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite.

The process for converting a feed stream, especially an oxygenate feed stream in the presence of a molecular sieve catalyst composition is carried out in a reactor process. In one embodiment, the reactor process is a fixed bed reactor process, a fluidized bed reactor process, preferably a continuous fluidized bed reactor process, and most preferably a continuous high velocity fluidized bed reactor process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred oxygenate-to-olefin reactor is a riser reactor. Riser reactors are generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor, a regenerator, and a recovery system.

The reactor or reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Feed stream, preferably an oxygenate feed stream, optionally with one or more diluent(s), is fed to the one or more riser reactor(s) in which a zeolite, zeolite-type molecular sieve catalyst, silicaluminophosphate catalyst composition or coked version thereof is introduced. In one embodiment, the molecular sieve catalyst composition or coked version thereof is contacted with a liquid or gas, or combination thereof, prior to being introduced to the riser reactor(s). Preferably, the liquid is water or methanol, and the gas is an inert gas such as nitrogen.

In an embodiment, the feed stream, preferably an oxygenate feed stream, is feed into the reactor in the vapor form or the liquid form. The vapor form of the feed stream is referred to as a vapor feed stream. The feed stream in the liquid form is referred to as the liquid feed stream. The amount of liquid feed stream fed separately or jointly with a vapor feed stream, to a reactor system is in the range of from 0.1 weight percent to about 85 weight percent, preferably from about 1 weight percent to about 75 weight percent, more preferably from about 1 weight percent to about 10 weight percent based on the total weight of the feed stream including any diluent contained therein. The liquid and vapor feed streams are preferably of similar composition, or contain varying proportions of the same or different feed stream compositions with varying proportions of the same or different diluent compositions.

The feed stream, preferably an oxygenate feed stream, entering the reactor system is preferably converted, partially or fully, in the first reactor zone into a reactor effluent stream that enters the disengaging vessel along with a coked molecular sieve catalyst composition. In the preferred embodiment, particle size separators within the disengaging vessel are designed to separate catalyst particles from the reactor effluent stream containing one or more olefin(s) within the disengaging zone as well as separate catalyst particles from catalyst fines entrained in the reactor effluent stream. Cyclones are preferred particle size separators. Cyclones generally retain catalyst particles but do not retain catalyst fines.

Gravity effects within the disengaging vessel will also separate the catalyst particles from the reactor effluent stream. Other methods for separating the catalyst particles from the reactor effluent stream include the use of plates, caps, elbows, and the like.

In one embodiment, the reactor effluent stream as it leaves the reactor comprises ethylene and propylene, $C_4$+olefins, methane, $C_2$+parafins, water, unreacted oxygenate feed stream, and oxygenate hydrocarbons. In another embodiment, the reactor effluent stream comprises from about 30 wt. % to about 70 wt. % water, preferably, from about 35 wt. % to about 70 wt. % water; more preferably from about 40 wt. % to about 65 wt. % water expressed as a percentage of the total weight of the reactor effluent stream. According to another aspect of the invention, there are catalyst fines entrained in the reactor effluent stream. The weight of catalyst in the reactor effluent stream, including catalyst fines, expressed as a percent of the weight of the reactor effluent stream plus entrained catalyst comprises about 5 wt. % or less, preferably about 2 wt. % or less, more preferably about 1 wt. % or less; even more preferably about 0.5 wt. % or less. In another embodiment, the weight of the catalyst, including catalyst fines, expressed as a percentage of the weight of the reactor effluent stream plus entrained catalyst comprises from about 0.00005 wt. % to about 0.5 wt. %; preferably; from about 0.0001 wt. % to about 0.1 wt. %.

In another embodiment, about 10 wt. % or less, preferably about 5 wt. % or less, most preferably about 1 wt. % or less of the catalyst fines in the reactor effluent stream has a particle size greater than 40 microns, based upon the total weight of catalyst fines in the reactor effluent stream.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from about 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C., and most preferably from about 350° C. to about 550° C.

The conversion pressure employed in the conversion process, specifically within the reactor system, varies over a wide range including autogenous pressure. The conversion pressure is based on the partial pressure of oxygenate in the oxygenate feed stream exclusive of any diluent therein. Typically, the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting an oxygenate feed stream in the presence of a molecular sieve catalyst composition within a reaction zone, is defined as the total weight of the oxygenate feed stream excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of an oxygenate feed stream containing methanol and dimethyl ether is in the range of from about 20 $hr^{-1}$ to about 300 $hr^{-1}$.

The superficial gas velocity (SGV) of an oxygenate feed stream including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate-to-olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See, for example, U.S. Pat. No. 5,952,538 that is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The process of converting oxygenates to olefins with certain molecular sieve catalyst compositions causes carbonaceous deposits or "coke" to build up on the catalyst. In one embodiment, the cooked molecular sieve catalyst or coked catalyst is withdrawn from a disengaging vessel of the reactor, preferably by one or more cyclones(s). The coked catalyst is introduced into a regenerator. In the regenerator, the cooked catalyst is contacted with a regeneration medium, preferably a gas containing oxygen, under general regeneration conditions of temperature, pressure, and residence time.

Non-limiting examples of the regeneration medium include one or more of oxygen, $0_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The preferred residence time of a catalyst, including a molecular sieve catalyst, in the regenerator is in the range of from about one minute to several hours, most preferably about one minute to about 100 minutes. In one embodiment, the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with coked catalyst. Also, in another embodiment, fresh molecular sieve catalyst is added to the regenerator containing a regeneration medium of oxygen and water as described in U.S. Pat. No. 6,245,703, which is herein fully incorporated by reference.

According to one embodiment, the burning of catalyst including catalyst particles in the regenerator produces a flue gas and regenerated catalyst, including regenerated catalyst particles and regenerated catalyst fines. The flue gas is defined as the gaseous output of the regenerator. The flue gas is separated from the regenerated catalyst particles by a particle size separator such as a cyclonic separator or cyclone. The cyclones retain catalyst particles but allow the flue gas to exit the regenerator. Additionally, regenerated catalyst fines are carried in the flue gas and leave the regenerator.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst from the regeneration system and passing the regenerated catalyst through a catalyst cooler that forms a cooled regenerated catalyst. The catalyst cooler, in an embodiment, is a heat exchanger that is located either internal or external to the regeneration system.

In one embodiment, the cooler regenerated catalyst is returned to the regenerator in a continuous cycle, alternatively, (see U.S. patent application Ser. No. 09/587,766 filed Jun. 6, 2000) a portion of the cooled regenerated catalyst is returned to the regenerator vessel in a continuous cycle, and another portion of the cooled regenerated catalyst is returned to the riser reactor(s), directly or indirectly, or a portion of the regenerated catalyst or cooled regenerated catalyst is contacted with by-products within the reactor effluent stream (PCT WO 00/49106 published Aug. 24, 2000), which are all herein fully incorporated by reference. In another embodiment, a regenerated catalyst contacted with an alcohol, preferably ethanol, 1-propanol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are in disclosed U.S. Pat. No. 6,290,916 (controlling moisture), which is herein fully incorporated by reference.

The regenerated catalyst particles are withdrawn from the regenerator and returned to the reactor. In one embodiment, the regenerated catalyst particles that are withdrawn from the regeneration system, preferably from the catalyst cooler, are combined with a fresh catalyst and/or re-circulated catalyst and/or feed stream and/or fresh gas or liquids, and returned to the riser reactor(s). In another embodiment, the regenerated catalyst withdrawn from the regeneration system is returned to the riser reactor(s) directly, optionally after passing through a catalyst cooler. In one embodiment, a carrier, such as an inert gas, vapor feed stream, steam or the like, semi-continuously or continuously, facilitates the introduction of the regenerated catalyst to the reactor or reactor system, preferably to the one or more riser reactor(s).

In one embodiment, the optimum level of coke on the catalyst composition in the reaction zone is maintained by controlling the flow of the regenerated catalyst or cooled regenerated catalyst from the regeneration system to the reactor system. There are many techniques for controlling the flow of a catalyst described in Michael Louge, *Experimental Techniques, Circulating Fluidized Beds*, Grace, Avidan and Knowlton, eds., Blackie, 1997 (336–337), which is herein incorporated by reference. This is referred to as the complete regeneration mode. In another embodiment, the optimum level of coke on the molecular sieve catalyst in the reaction zone is maintained by controlling the flow rate of the oxygen-containing gas flow to the regenerator. This is referred to as the partial regeneration mode.

Coke levels, or the level of carbonaceous deposits on the catalyst, are measured by withdrawing from the conversion process the catalyst composition at a point in the process and determining its carbon content.

In one preferred embodiment, the catalyst in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of catalyst. See for example U.S. Pat. No. 6,023,005, which is herein fully incorporated by reference. It is recognized that the catalyst in the reaction zone is made up of a mixture of regenerated catalyst and catalyst that has ranging levels of carbonaceous deposits. The measured level of carbonaceous deposits thus represents an average of the levels an individual catalyst particle.

As noted above, the reactor effluent stream leaves the reactor through particle size separators. The reactor effluent stream optionally passes through a heat exchanger system. According to one embodiment the heat exchanger system comprises one or more heat exchangers, preferably two to four heat exchangers, most preferably two or three heat exchangers. Optionally, the heat exchanger system cools the reactor effluent stream to produce a cooled effluent stream. The cooled effluent stream is withdrawn from the heat exchanger system and is sent to a quench device.

Reactor Effluent Quenching

The oxygenate-to-olefin process forms a substantial amount of water as a byproduct. Furthermore, a substantial amount of catalysts are carried in the reactor effluent stream. Water and catalyst fines can be removed from the reactor effluent stream by a quench device. A "quench device" is a device for removing a portion of the reactor effluent stream by establishing a sufficient quantity of a liquid phase in contact with the reactor effluent stream which condenses at least a portion of the material in the reactor effluent stream. One example of a quench device in an oxygenate-to-olefin product stream is found in U.S. Pat. No. 6,121,504 (direct product quench). The liquid matter that contacts the reactor effluent stream and causes the condensation is called a "quench medium."

In a quench device, at least a portion of the reactor effluent stream is rapidly condensed through contact with a quench medium in the liquid state (a form of what is typically called "direct contact heat transfer"). When quenching in a quench device, at least a portion of the reactor effluent stream remains in a gaseous state. A portion of the reactor effluent stream condenses to form a liquid fraction which is withdrawn from the quench device as a first liquid stream in one embodiment. The portion of the reactor effluent stream in a gaseous state is separated from the liquid fraction.

The portion of the reactor effluent stream that is gaseous under quenching conditions typically comprises prime olefins, dimethyl ether, methane, CO, $CO_2$, ethane, propane, and any water and unreacted oxygenate feed stream that is not condensed during the operation of the quench device. These gaseous compounds in the reactor effluent stream generally pass through the quench device and form the quenched effluent stream. The quenched effluent stream is defined as the effluent stream after at least one stage of quenching. The compounds in the reactor effluent stream that are liquid under quenching conditions typically comprises water, a portion of the unreacted oxygenate feed stream (typically methanol), and a small portion of the oxygenate conversion byproducts, e.g. heavy hydrocarbons ($C_5$+). These compounds form a quench bottoms stream or a liquid fraction. Additionally, quench medium contacts the catalyst fines in the reactor effluent stream and washes the catalyst fines into the liquid fraction. Thus, the liquid fraction contains catalyst fines.

According to one embodiment of the present invention, a quench tower is employed as a quench device. According to one embodiment the quench device has one or more stages, preferably one to four stages, most preferably one to three stages. A one stage quench is disclosed in U.S. Pat. No. 6,121,504, the content of which is incorporated fully by reference. A two stage quench is disclosed in U.S. Pat. No. 6,403,854, the content of which is incorporated fully by reference.

In a particular embodiment, the quench medium is water. In another embodiment, the quench medium is a portion of the water that has been recovered from the quench device and cooled (thus reintroduced to the quench tower), and which contains at least a portion of the catalyst fines separated from the gaseous portion of the reactor effluent stream and is referred to as recovered quench medium. According to one embodiment, the quench is operated under conditions such that the cooled process gas then enters the quench device where effluent water is condensed, acetic acid is neutralized and some heavy oxygenates ($C_3$–$C_4$+aldehydes, ketones & alcohols) are rejected.

As previously described the reactor effluent stream is quenched to remove catalyst fines and water that are present in the reactor effluent stream and produces a quenched effluent stream.

In an embodiment of the invention, the quenched effluent stream contains both ethylene and propylene. Desirably, the quenched effluent stream contains about 50 wt. % or more, preferably from about 50 wt. % to about 95 wt. %, more preferably from about 55 wt. % to about 90 wt. %, and most preferably from about 60 wt. % to about 85 wt. % ethylene and propylene based upon the total weight of the quenched effluent stream as it leaves the quench device.

In another embodiment, the quenched effluent stream comprises about 25 wt. % or more from about 25 wt. % ethylene to about 75 wt. %, more preferably from about 30 wt. % to about 60 wt. %, and most preferably from about 35 wt. % to about 50 wt. % ethylene based upon the total weight of the quenched effluent stream after it leaves the quench device.

In another embodiment, the quenched effluent stream comprises about 20 wt. % or more, preferably from about 20 wt. % to about 70 wt. %, more preferably from about 25 wt. % to about 50 wt. %, and most preferably from about 30 wt. % to about 40 wt. % propylene based upon the total weight of the quenched effluent stream after it leaves the quench device.

It is desirable that the quenched effluent stream contains a relatively low concentration of ethane, preferably a lower concentration of ethane than propane. Preferably, the quenched effluent stream comprises about 4 wt. % or less, more preferably about 3 wt. % or less, and most preferably about 2 wt. % or less ethane based upon the total weight of the quenched effluent stream after it leaves the quench device.

It is also desirable that the quenched effluent stream contains a relatively low concentration of propane. Preferably, the quenched effluent stream comprises about 5 wt. % or less, more preferably about 4 wt. % or less, and most preferably about 3 wt. % or less propane based upon the total weight to the quenched effluent stream after it leaves the quench device.

In one embodiment, the quenched effluent stream that is provided comprises about 50 wt. % or less, preferably about 20 wt. % or less, more preferably about 10 wt. % or less, and most preferably about 5 wt. % or less dimethyl ether. In an embodiment, the provided olefins stream will contain at about 100 wppm or more, preferably about 500 wppm dimethyl ether or more, and more preferably about 1,000 wppm or more dimethyl ether based upon the total weight of the quenched effluent stream as it leaves the quench device.

In another embodiment of the invention, the quenched effluent stream is further processed by compression, preferably multi-staged compression. Two, three, four or more stages can be used, with two or three stages being preferred.

Desirably, the quenched effluent stream is compressed to a pressure that is greater than that at which the oxygenate-to-olefin reaction process is carried out. Preferably, the quenched effluent stream is compressed to a pressure of about 30 psia (207 kPa) or more, more preferably about 50 psia (345 kPa) or more, most preferably about 100 psia (689 kPa) or more. High-pressure ranges are particularly preferred, with the upper limit being a practical one based on cost of design and ease of operation. In an embodiment, the pressure is from about 1,000 psia (6,895 kPa) to about 5,000 psia (34,450 kPa), preferably from about 750 psia (5171 kPa) to about 5,000 psia (34,450 kPa), more preferably from about 500 psia (3447 kPa) to about 5,000 psia (34,450 kPa).

Following compression, the quenched effluent stream is further processed by washing to remove acid gases and alternatively other oxygenates and drying to remove water as described below.

Washing and Drying

An acid gas wash optionally is used to remove acid gas from the quenched effluent stream in the first fraction by contacting the first fraction with an acid gas absorbent or adsorbent. Non-limiting examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred.

Aqueous amine solutions, which are useful in one embodiment this invention, contain any amine compound or compounds suitable for acid gas absorption. Non-limiting examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations range from about 0.5 to about 8 moles of amine per liter of aqueous solution in one embodiment.

Piperazine and/or monomethylethanolamine (MMEA) in one embodiment are added to aqueous amine solutions to enhance their absorption capabilities. These additives are included in the aqueous solution at a concentration of from about 0.04 to about 2 moles per liter of aqueous solution.

Caustic compounds, which are used in one embodiment of this invention, are alkaline compounds, which are effective in removing acid gas from an olefin containing stream. Non-limiting examples of such alkaline compounds include sodium hydroxide and potassium hydroxide.

Following acid gas treating, it is desirable to remove additionally entrained material in the quenched effluent stream using a water wash. Conventional equipment is optionally used. It is desirable, however, to further remove additional water from the quenched effluent streams.

This invention further includes an optional drying embodiment. In this embodiment, a solid or liquid drying system is used to remove water and/or additional oxygenated hydrocarbon from the quenched effluent stream.

In the solid drying system, the quenched effluent stream having been optionally acid gas treated and water washed, is contacted with a solid adsorbent to further remove water and oxygenated hydrocarbon to very low levels. Typically, the adsorption process is carried out in one or more fixed beds containing a suitable solid adsorbent.

Adsorption is useful for removing water and oxygenated hydrocarbons to very low concentrations, and for removing oxygenated hydrocarbons that are not normally be removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of contaminants being removed. Non-limiting examples of solid adsorbents for removing water and various polar organic compounds, such as oxygenated hydrocarbons and absorbent liquids, include aluminas, silica, 3A molecular sieves, 4A molecular sieves, and alumino-silicates. Beds containing mixtures of these sieves or multiple beds having different adsorbent solids optionally is used to remove water, as well as a variety of oxygenated hydrocarbons.

In one embodiment of this invention, one or more adsorption beds is arranged in series or parallel. In one example of a series arrangement, a first bed is used to remove the smallest and most polar molecules, which are the easiest to remove. Subsequent beds for removing larger less polar oxygenated species are next in series. As a specific example of one type of arrangement, water is first selectively removed using a 3A molecular sieve. This bed is then followed by one or more beds containing one or more less selective adsorbents such as a larger pore molecular sieve e.g. 13X and/or a high surface area active alumina such as Selexorb CD (Alcoa tradename).

In another embodiment, the first bed is a 3.6A molecular sieve capable of selectively removing both water and methanol. This bed is then followed by one or more 13X or active alumina beds as described above.

The adsorbent beds typically are operated at ambient temperature or at elevated temperature as required, and with either upward or downward flow. Regeneration of the adsorbent materials are often carried out by conventional methods including treatment with a stream of a dry inert gas such as nitrogen at elevated temperature.

In the liquid drying system, a water absorbent is used to remove water from the quenched effluent stream. The water absorbent of one embodiment is any liquid effective in removing water from an olefin containing stream. Preferably, the water absorbent is a polyol or an alcohol, such as ethanol or methanol.

Preferably the olefin from the adsorption beds contains less than about 100 wppm water, more preferably less than about 10 wppm, and most preferably less than 1 wppm. Preferably less than about 10 wppm dimethyl ether is present in the stream leaving the adsorption beds, more preferably less than about 5 wppm, and most preferably less than about 1 wppm. The step of acid washing and drying produces an olefin stream.

Olefin Product Recovery

The olefin stream from the dryer is further processed to isolate and purify components in the washed effluent stream, particularly, olefin product streams containing prime olefins (i.e. ethylene, propylene, and butylene). There are many well-known recovery systems, techniques and sequences that are useful in separating and purifying an olefin stream into one or more olefin product streams, preferably, high purity olefin product streams.

As noted the object of one embodiment of the present invention is to isolate prime olefin product streams that contains a $C_x$ olefin, wherein x is an integer from 2 to 4, in an amount that is about 80 wt. % or more, preferably about 90 wt. % or more, more preferably about 95 wt. % or more based upon the total weight of the high purity prime olefin stream. It is most preferable to isolate high purity prime olefin streams that contain $C_x$ olefin, wherein x is an integer from 2 to 4, in an amount greater than about 99 wt. % or more, based on the total weight of the high purity olefin stream. The olefin product stream has a purity grade that is selected for the particular application or end use of the olefin product stream. To accomplish the isolation of prime olefin streams, and preferably high purity prime olefin streams, a fractionation train is provided. The fractionation train comprises a demethanizer, a $C_2$ splitter, a deethanizer, a $C_3$ splitter, a depropanizer, a debutanizer, and a debutyleneizer. A demethanizer is a fractionation tower that separates methane and compounds with a boiling point lower than methane from ethylene and compounds with boiling point higher than ethylene. A $C_2$ splitter is a fractionation tower that separates ethylene and compounds with a boiling point lower than ethylene from ethane and compounds with boiling point higher than ethane. A deethanizer is a fractionation tower that separates ethane and compounds with a boiling point lower than ethane from propylene, and compounds with boiling point higher than propylene. A $C_3$ splitter is a fractionation tower that separates propylene and compounds with a boiling point lower than propylene from propane and compounds with boiling point higher than propane.

A depropanizer is a fractionation tower that separates propane and compounds with a boiling point lower than propane from butylene and compounds with boiling point higher than butylene. A debutyleneizer is a fractionation tower that separates butylene and compounds with a boiling point lower than butane from butane and compounds with boiling point higher than butane.

As noted, the dried olefin stream contains other byproducts. The byproducts, in one embodiment, need to be removed from the final olefin product streams. Alkynes and dienes are byproducts of the oxygenate-to-olefin reaction and are typically not found, in significant amounts, in the final olefin product streams.

Hydrogenation is a way of eliminating alkynes and/or dienes from the olefin product stream. Hydrogenation reacts an unsaturated hydrocarbon, such as an alkyne and/or diene with hydrogen to hydrogenate. Preferably, in the case of hydrogenation of an alkyne, the triple bond in the alkyne is saturated by adding one hydrogen molecule across the triple bond resulting in a double bond—i.e. an olefin. In the case a diene, one of the two double bonds is saturated by adding one hydrogen molecule across one of the double bonds resulting in one double bond—i.e. an olefin. Hydrogenation units include without limitation acetylene converters and methyl acetylene and/or propadiene converters. There are types of acetylene converters distinguished by their location relative to a demethanizer. Front-end acetylene converters are located before the demethanizer. Back-end acetylene converters, are located after the demethanizer. Front-end acetylene converters convert acetylene in the presence of indigenous hydrogen. Indigenous hydrogen is hydrogen that is produced as a byproduct of the oxygenate-to-olefin reaction and was not removed from the olefin stream. Back-end acetylene converters convert acetylene to ethylene after the demethanizer. The demethanizer separates any indigenous hydrogen that was produced as a byproduct from the oxygenate-to-olefin reaction from the ethylene and higher boiling point compounds. Thus, in a back end acetylene converter a hydrogen source must be added to the olefin stream before hydrogenation of the alkynes and/or dienes. The hydrogen source, in one embodiment, is in whole, or in part, separated from the olefin stream. The hydrogen source stream, of one embodiment comprises in whole, or in part, hydrogen produced from the oxygenate-to-olefin reaction. The hydrogen source in another embodiment is produced from decomposition of methanol and/or other oxygenates optionally followed by shifting the carbon monoxide produced from oxygenate decomposition to hydrogen by reaction with water.

The olefin stream, for the purpose of this invention is the feed stream to the hydrogenation unit. The olefin stream in one embodiment is an ethylene stream. In another embodiment, the olefin stream is a propylene stream. In still another embodiment, the olefin stream is a butylene stream. In one embodiment, the olefin stream is a first olefin stream and contains any combination of ethylene, propylene and/or butylene. In one embodiment, the first olefin stream contains about 50 mol. % or more, preferably about 90 mol. % or more, more preferably about 98 mol. % or more, most preferably about 95 mol. % or more olefin based upon the composition of the first olefin stream. In one embodiment, the first olefin stream comprises about 25 mol. % or more, preferably about 90 mol. % or more, most preferably about 98 mol. % or more ethylene based upon the composition of the first olefin stream. In another embodiment, the first olefin stream comprises about 25 mol. % or more, preferably about 90 mol. % or more, most preferably about 95 mol. % or more propylene based upon the composition of the first olefin stream.

In still another embodiment, there are about 500 mppm or less, typically about 200 mppm, more typically about 50 mppm or less alkynes and/or dienes in the first olefin stream based upon the composition of the first olefin stream. In still another embodiment, the alkynes and/or dienes are acetylene and the first olefin stream comprises about 500 mppm or less, typically about 200 mppm, more typically about 50 mppm or less acetylene based upon the composition of the first olefin stream. In another embodiment, the alkynes and/or dienes are methyl acetylene and/or propadiene and the first olefin stream comprises about 500 mppm or less, typically about 200 mppm, more typically about 50 mppm or less methyl acetylene and/or propadiene based upon the composition of the first olefin stream.

As noted, the first olefin stream of one embodiment, comprises indigenous hydrogen. In one embodiment, the first olefin stream comprises indigenous hydrogen in an amount ranging from about 0.1 mol. % to about 1.0 mol. %, preferably from about 0.2 mol. % to about 0.6 mol. % indigenous hydrogen based upon the composition of the first olefin stream.

In another embodiment, hydrogen is added to the first olefin stream as shown in FIG. 2. Hydrogen source stream flows along line 26 and is combined with the first olefin stream flowing along line 20. In one embodiment, the hydrogen source stream is from a source selected from the group comprising pipeline hydrogen, hydrogen from reformed naphtha, hydrogen from refinery streams, hydrogen from bottled sources, hydrogen from water electrolysis reactors, hydrogen from refinery streams, hydrogen from methanol decomposition and hydrogen from the oxygenate-to-olefin process that was removed from the olefin stream. In yet another embodiment, the added hydrogen is from a hydrogen source stream having about 90 mol. % or more, preferably from about 95 mol. % or more, more preferably about 98 mol. % or more, most preferably about 99 mol. % or more hydrogen based upon the composition of the hydrogen source stream.

In an embodiment, the hydrogen source stream and the olefin stream combine to form a combined stream that flows along line 27. In one embodiment, the combined stream or the first olefin stream has about 500 mppm or less, preferably about 400 mppm or less, more preferably about 300 mppm or less methane based upon the composition of the respective combined stream or first olefin stream. In one embodiment, the combined stream or the first olefin stream has about 500 mppm or less, preferably about 400 mppm, more preferably about 300 mppm or less methane and nitrogen based upon the composition of the respective combined stream or the first olefin stream. In another embodiment, the combined stream or the first olefin stream has about 1 mppm or less CO based upon the composition of the respective combined stream or first olefin stream. In still another embodiment, the combined stream, the first olefin stream or the hydrogen source stream has about 1 mppm or less $CO_2$ based upon the composition of the respective combined stream, first olefin stream or hydrogen source stream.

According to one embodiment, excess hydrogen from the hydrogen source stream is added to the first olefin stream. Particularly, about 1.05 moles or more of hydrogen, preferably from about 1.5 moles to about 50 moles of hydrogen, more preferably from about 1.5 moles to about 10 moles of hydrogen is added for every mole of alkynes and/or dienes in the first olefin stream.

According to an embodiment, the first olefin stream and/or the combined stream is heated, preferably with the third olefin stream in a heat exchanger. The first olefin stream travels along line 20 and passes through a first heat exchanger 22 and a second heat exchanger 24. The first heat exchanger 22 and/or second heat exchanger 24 heat the first olefin stream to a desired temperature. Optionally and alternatively, the first heat exchanger 22 and/or second heat exchanger are located on line 27 and heat the combined olefin stream. According to one embodiment, the first olefin stream and/or the combined olefin stream are heated to a temperature ranging from about 100° F. (38° C.) to about 250° F. (121° C.), preferably from about 120° F. (49° C.) to about 200° F. (93° C.), more preferably from about 150° F. (66° C.) to about 190° F. (88° C.).

As noted the first olefin stream and/or combined olefin stream are hydrogenated in a first hydrogenation step. The hydrogenation step converts alkynes and/or dienes, such as acetylene, methyl acetylene, and/or propadiene to olefins. A competing reaction occurs that converts olefins to paraffins. Thus, it is desirable in one embodiment that the conditions for the reaction favor the reaction of converting alkynes and/or dienes to olefins rather than converting the olefins to paraffins. If the latter reaction is favored, an unacceptable level of alkynes and/or dienes is likely to remain in the olefin stream after the first hydrogenation step. This is due particularly to the high amount of olefin product by volume relative to amount of olefin by volume in the first olefin stream and/or combined olefin stream.

According to one embodiment, the catalyst that is used in the first hydrogenation step ("first catalyst") is selected from the group consisting of Group VIII metal hydrogenation catalysts. See U.S. Patent Nos. 3,679,762, 4,571,442, 4,347,392, 4,128, 595, 5,059,732, and 4,762,956 for examples of hydrogenation reactors and hydrogenation catalyst—all of these references are fully incorporated by reference into the present application. Preferably the first catalyst is an elemental Group VIII metal catalysts or combinations thereof. By elemental it is meant a catalyst that contains the identified element whether in its pure form or in the form of a salt. More preferably, the first catalyst is an elemental noble metal catalyst on a silica and/or alumina substrate with a co-catalyst selected from the group consisting of elemental silver, vanadium or iodine or combinations thereof.

According to one embodiment, the first hydrogenation step occurs at a pressure ranging from about 50 psia (344 kPaa) to about 400 psia (2760 kPaa), preferably from about 200 psia (1380 kPaa) to about 300 psia (2070 kPaa), and more preferably from about 250 psia (1720 kPaa) to about 300 psia (2070 kPaa). With reference to FIG. 2, the combined olefin stream of one embodiment is transported along line 27 into a first reactor 28. The first reactor 28 contains a first catalyst. It produces a second olefin stream that is withdrawn from the first reactor 28 along line 30. The second olefin stream is defined as the olefin stream after one hydrogenation step. The second olefin stream comprises about 10 mppm or less, preferably about 5 mppm or less, more preferably about 2 mppm or less alkyne based upon the composition of the second olefin stream. In one embodiment, the alkyne is acetylene. In another embodiment, the alkyne is methyl acetylene and/or propadiene.

In another embodiment, the amount of hydrogen in the second olefin stream is from about 100 mppm to about 1000 mppm, preferably from about 50 mppm to about 250 mppm, most preferably from about 10 mppm to about 100 mppm based upon the weight of the second olefin stream.

As shown in FIG. 2, the second olefin stream travels along line 30 to a third (and optional) heat exchanger 32. The third heat exchanger 32 is capable of heating or cooling the second olefin stream as needed to adjust the temperature of the second olefin stream before a second hydrogenation step. According to an embodiment, the temperature of the second olefin stream ranges from about 100° F. (38° C.) to about 250° F. (121° C.), preferably from about 120° F. (49° C.) to about 200° F. (93° C.), more preferably from about 150° F. (66° C.) to about 190° F. (88° C.) before the second hydrogenation step.

According to another embodiment, second hydrogenation step occurs at a pressure ranging from about 50 psia (344 kPaa) to about 400 psia (2760 kPaa), preferably from about 200 psia (1380 kPaa) to about 300 psia (2070 kPaa), and more preferably from about 250 psia (1720 kPaa) to about 300 psia (2070 kPaa).

According to one embodiment, the catalyst in the second hydrogenation step ("second catalyst") is an elemental Group VIII metal catalysts or combinations thereof. By elemental it is meant a catalyst that contains the identified element whether in its pure form or in the form of a salt. More preferably, the second catalyst is an elemental noble metal catalyst on a silica and/or alumina substrate with a co-catalyst consisting of elemental nickel and/or iron. In one embodiment, the second catalyst is the same as the first catalyst. With continued reference to FIG. 2, the second olefin stream passes along line 30 into the second hydrogenation reactor 34 for a second hydrogenation step. The purpose of the second hydrogenation step, according to one embodiment, is to chemically react all remaining hydrogen so that below acceptable levels of hydrogen remains after the second hydrogenation step. The second hydrogenation step is typically non-selective so that the remaining hydrogen reacts with olefin as well as alkynes and dienes. The second hydrogenation reactor 34 contains the second hydrogenation catalyst.

In an alternative embodiment, the second hydrogenation step occurs in the same reaction vessel as the first hydrogenation step. In such an embodiment, not illustrated in FIG. 2 a reactor has a first hydrogenation bed comprising a first hydrogenation catalyst and a second hydrogenation bed containing a second hydrogenation catalyst.

The second hydrogenation step produces a third olefin stream or hydrogenated olefin stream.

The third olefin stream is defined as the olefin stream after two steps of hydrogenation and is withdrawn along line 36. The third olefin stream comprises olefins such as prime olefins (i.e. ethylene, propylene, and/or butylene). In one embodiment, the amount of hydrogen in the third olefin stream is about 20 mppm or less, preferably about 10 mppm or less, more preferably about 5 mppm or less, most preferably about 1 mppm or less, based upon the composition of the third olefin stream. According to one embodiment, the amount of alkynes and/or dienes is about 5 mppm or less, preferably about 1 mppm or less, more preferably about 0.5 mppm or less. According to one embodiment, about 1 mol. % or less, more preferably about 500 mppm or less, even more preferably about 200 mppm or less and most preferably about 100 mppm or less of the olefins are hydrogenated in the first and second step based upon the composition of the first olefin stream. According to one embodiment, about 1 mol. % or less, more preferably about 500 mppm or less, even more preferably about 200 mppm or less and most preferably about 100 mppm or less ethylene are hydrogenated in the first and second step based upon the composition of the first olefin stream. According to one embodiment, about 1 mol. % or less, more preferably about 500 mppm or less, even more preferably about 200 mppm or less and most preferably about 100 mppm or less propylene are hydrogenated in the first and second step based upon the composition of the first olefin stream. According to one embodiment, a single step of reacting reacts to preferentially eliminate all alkynes and/or dienes over olefins and chemically reacts all remaining hydrogen and conditions described above for the first reaction step and/or the second reaction step.

According to an embodiment referenced in FIG. 2, the third olefin stream leaves the second reactor along line 36 and passes through the first heat exchanger 22 where the third olefin stream is optionally cooled by the first olefin stream. In another step, the olefin stream passes through a fourth (and optional) heat exchanger 38 referred to as a fourth heat exchanger 38. The fourth heat exchanger 38 further cools the olefin stream. According to one embodiment, the cooling step is cryogenic. Thereafter, the third olefin stream continues to a fractionation step to further fractionate the olefin stream into product streams according to established principles of olefin fractionation.

Olefin Product Use

Suitable well-known reaction systems that follow the recovery system primarily take lower value products and convert them to higher value products. For example, the $C_4$ hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel.

Non-limiting examples of reaction systems that take lower value products and convert them to higher value products include U.S. Pat. No. 5,955,640 (converting a four carbon product into butene-1), U.S. Pat. No. 4,774,375 (isobutane and butene-2 alkylated to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading $C_3$, $C_4$ and $C_5$ Olefinic Streams*, Pet. & Coal, Vol. 37, No. 4 (1995) (dimerizing or oligomerizing propylene, butylene and pentylene), which are all herein fully incorporated by reference.

Other uses for one or more olefin products are disclosed in U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent stream fed to another reactor) PCT WO 01/60770 published Aug. 23, 2001 and U.S. patent application Ser. No. 09/627,634 filed Jul. 28, 2000 (high-pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In another embodiment, olefin(s) produced are directed to, in one embodiment, one or more polymerization processes for producing various polyolefins. (See for example U.S. patent application Ser. No. 09/615,376 filed Jul. 13, 2000 that is herein fully incorporated by reference.)

Polymerization processes include solution, gas phase, slurry phase and a high-pressure process, or a combination thereof. Particularly preferred is a gas phase or a slurry phase polymerization of one or more olefin(s) at least one of which is ethylene or propylene. Polymerization processes include those non-limiting examples described in the following: U.S. Pat. Nos. 4,543,399, 4,588,790, 5,028,670, 5,317,036, 5,352,749, 5,405,922, 5,436,304, 5,453,471, 5,462,999, 5,616,661, 5,627,242, 5,665,818, 5,677,375, 5,668,228, 5,712,352 and 5,763,543 and EP-A-0 794 200, EP-A-0 802 202, EP-A2-0 891 990 and EP-B-0 634 421 describe gas phase polymerization processes; U.S. Pat. Nos. 3,248,179 and 4,613,484, 6,204,344, 6,239,235 and 6,281,300 describe slurry phase polymerization processes; U.S. Pat. Nos. 4,271,060, 5,001,205, 5,236,998 and 5,589,555 describe solution phase polymerization processes; and U.S. Pat. Nos. 3,917,577, 4,175,169, 4,935,397, and 6,127,497 describe high-pressure polymerization processes; all of which are herein fully incorporated by reference.

These polymerization processes utilize a polymerization catalyst that optionally includes any one or a combination of the molecular sieve catalysts discussed above. However, the preferred polymerization catalysts are those Ziegler-Natta, Phillips-type, metallocene, metallocene-type and advanced polymerization catalysts, and mixtures thereof. Non-limiting examples of polymerization catalysts are described in U.S. Pat. Nos. 3,258,455, 3,305,538, 3,364,190, 3,645,992, 4,076,698, 4,115,639, 4,077,904 4,482,687, 4,564,605, 4,659,685, 4,721,763, 4,879,359, 4,960,741, 4,302,565, 4,302,566, 4,302,565, 4,302,566, 4,124,532, 4,302,565, 5,763,723, 4,871,705, 5,120,867, 5,324,800, 5,347,025, 5,384,299, 5,391,790, 5,408,017, 5,491,207, 5,455,366, 5,534,473, 5,539,124, 5,554,775, 5,621,126, 5,684,098, 5,693,730, 5,698,634, 5,710,297, 5,714,427, 5,728,641, 5,728,839, 5,753,577, 5,767,209, 5,770,753 and 5,770,664, 5,527,752, 5,747,406, 5,851,945 and 5,852,146, all of which are herein fully incorporated by reference.

In preferred embodiment, the present invention comprises a polymerizing process of one or more olefin(s) in the presence of a polymerization catalyst system in a polymerization reactor to produce one or more polymer products, wherein the one or more olefin(s) having been made by converting an alcohol, particularly methanol, using a zeolite or zeolite-type molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kPag) to greater than about 1000 psig (3448 kPag), preferably in the range of from about 200 psig (1379 kPag) to about 500 psig (3448kPag), and more preferably in the range of from about 250 psig (1724 kPag) to about 350 psig (2414 kPag). Typical conditions of polymerization temperature vary from about 0° C. to about 500° C., preferably from about 30° C. to about 350° C., more preferably in the range of from about 60° C. to 250° C., and most preferably in the range of from about 70° C. to about 150° C. In the preferred polymerization process the amount of polymer being produced per hour is greater than 25,000 lbs/hr (11,300 Kg/hr), preferably greater than 35,000 lbs/hr (15,900 Kg/hr), more preferably greater than 50,000 lbs/hr (22,700 Kg/hr) and most preferably greater than 75,000 lbs/hr (29,000 Kg/hr).

The polymers produced by the polymerization processes described above include linear low density polyethylene, elastomers, plastomers, high density polyethylene, low density polyethylene, polypropylene and polypropylene copolymers. The propylene-based polymers produced by the polymerization processes include atactic polypropylene, isotactic polypropylene, syndiotactic polypropylene, and propylene random, block or impact copolymers.

Typical ethylene based polymers have a density in the range of from 0.86 g/cc to 0.97 g/cc, a weight average molecular weight to number average molecular weight ($M_w/M_n$) of greater than 1.5 to about 10 as measured by gel permeation chromatography, a melt index ($I_2$) as measured by ASTM-D-1238-E in the range from 0.01 dg/min to 1000 dg/min, a melt index ratio ($I_{21}/I_2$) (I21 is measured by ASTM-D-1238-F) of from 10 to less than 25, alternatively a $I_{21}/I_2$ of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multi-layered constructions in the form of bottles, vessels, large hollow articles, rigid food containers and toys, etc.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

The foregoing description of the invention including but not limited to drawing and example are intended to illustrate one or more embodiments of the invention and are non-limiting. While the invention has been illustrated an described herein in terms of the advantages, features, and applications disclosed, it will be apparent to a person of ordinary skill in the art that the invention can be used in other instances. Other modifications and improvements can be made without departing from the scope of the invention.

The invention claimed is:

1. A process for hydrogenating byproducts selected from the group consisting of alkynes, dienes and mixtures thereof in an olefin product stream from an oxygenate-to-olefins reactor, the process comprising the steps of:
    (a) contacting an oxygenate with a molecular sieve catalyst in the oxygenate-to-olefins reactor to provide the olefin product stream;
    (b) isolating from the olefin product stream a first olefin stream containing 25 mol. % or more ethylene or 25 mol. % or more propylene, based upon the composition of the first olefin stream, and 500 mppm or less of the alkyne or diene byproduct;
    (c) hydrogenating the first olefin stream to produce a second olefin stream; and
    (d) hydrogenating the second olefin stream in the presence of from 100 mppm to 1000 mppm hydrogen, based upon the weight of the second olefin stream, to produce a third olefin stream containing 20 mppm or less hydrogen, based upon the composition of the third olefin stream.

2. The process of claim 1, wherein about 1.05 moles or more of hydrogen are present for every mole of alkyne or diene byproduct in the first olefin stream.

3. The process of claim 1, wherein from about 1.5 moles to about 50 moles of hydrogen are present for every mole of alkyne or diene byproduct in the first olefin stream.

4. The process of claim 1, wherein from about 1.5 moles to about 10 moles of hydrogen arc present for every mole of alkyne or diene byproduct in the first olefin stream.

5. The process of claim 1, further comprising heating the first olefin stream.

6. The process of claim 5, wherein the first olefin stream is heated to a temperature ranging from about 100° F. (38° C.) to about 250° F. (121° C.).

7. The process of claim 6, wherein the first olefin stream is heated to a temperature ranging from about 120° F. (49° C.) to about 200° F. (93° C.).

8. The process of claim 7, wherein the first olefin stream is heated to a temperature ranging from about 150° F. (66° C.) to about 190° F. (88° C.).

9. The process of claim 1, wherein hydrogenating the first olefin stream occurs at a pressure ranging from about 50 psia (344 kPaa) to about 400 psia (2760 kPaa).

10. The process of claim 9, wherein hydrogenating the first olefin stream occurs at a pressure ranging from about 200 psia (1380 kPaa) to about 300 psia (2070 kPaa).

11. The process of claim 10, wherein hydrogenating the first olefin stream occurs at a pressure ranging from about 250 psia (1720 kPaa) to about 300 psia (2070 kPaa).

12. The process of claim 1, wherein first olefin stream is hydrogenated in the presence of a first hydrogenating catalyst that is an elemental Group VIII metal catalyst.

13. The process of claim 12, wherein the first catalyst is an elemental noble metal on a substrate selected from the group consisting of silica, alumina and mixtures thereof with a co-catalyst selected from the group consisting of elemental silver, vanadium, iodine and combinations thereof.

14. The process of claim 12, wherein the first catalyst is an elemental palladium catalyst.

15. The process of claim 14, wherein the first catalyst is an elemental palladium catalyst on a substrate selected from the group consisting of silica, alumina and/or mixtures thereof with a co-catalyst selected from the group consisting of elemental silver, vanadium, iodine and combinations thereof.

16. The process of claim 1, wherein the first olefin stream is heated with the third olefin stream in a heat exchanger.

17. The process of claim 1, wherein the first olefin stream contains 50 mol. % or more olefin based upon the composition of the first olefin stream.

18. The process of claim 1, wherein the first olefin stream contains about 90 mol. % or more olefin based upon the composition of the first olefin stream.

19. The process of claim 1, wherein the first olefin stream contains about 98 mol. % or more olefin based upon the composition of the first olefin stream.

20. The process of claim 1, wherein the first olefin stream comprises about 200 mppm or less alkyne and or diene byproduct.

21. The process of claim 1, wherein the first olefin stream comprises about 90 mol. % or more propylene based upon the composition of the first olefin stream.

22. The process of claim 1, wherein the alkyne is methyl acetylene and the diene is propadiene and the first olefin stream comprises about 500 mppm or less byproducts based upon the composition of the first olefin stream.

23. The process of claim 1, wherein the temperature of the second olefin stream ranges from about 100° F. (38° C.) to about 250° F. (121° C.).

24. The process of claim 1, wherein the temperature of the second olefin stream ranges from about 120° F. (49° C.) to about 200° F. (93° C.).

25. The process of claim 1, wherein the temperature of the second olefin stream ranges from about 150° F. (66° C.) to about 190° F. (88° C.).

26. The process of claim 1, wherein the second olefin stream is hydrogenated at a pressure ranging from about 50 psia (344 kPaa) to about 400 psia (2760 kPaa).

27. The process of claim 1, wherein the second olefin scream is hydrogenated at a pressure ranging from about 200 psia (1380 kPaa) to about 300 psia (2070 kPaa).

28. The process of claim 1, wherein the second olefin stream is hydrogenated at a pressure ranging from about 250 psia (1720 kPaa) to about 300 psia (2070 kPaa).

29. The process of claim 1, wherein the second olefin stream is hydrogenated in the presence of a second hydrogenating catalyst that is an elemental Group VIII metal catalyst.

30. The process of claim 29, wherein the second catalyst is an elemental noble metal on a substrate selected from the group consisting of silica and/or alumina with a co-catalyst selected from the group comprising elemental iron catalyst, elemental nickel catalyst, and mixtures thereof.

31. The process of claim 30, wherein the second catalyst is an elemental palladium catalyst.

32. The process of claim 31, wherein the second catalyst is an elemental palladium catalyst on a substrate selected from the group consisting of silica, alumina and mixtures thereof with a co-catalyst selected from the group consisting of elemental iron, elemental nickel and mixtures thereof.

33. The process of claim 1, wherein the first olefin stream and the second olefin stream are hydrogenated in the presence of a first and second hydrogenation catalyst in which the first catalyst is the same as the second catalyst.

34. The process of claim 1, wherein the third olefin stream is converted to polyolefin.

* * * * *